(12) United States Patent
Yang et al.

(10) Patent No.: US 10,209,064 B2
(45) Date of Patent: Feb. 19, 2019

(54) ONLINE MEASURING METHOD OF CONCENTRATION AND DIAMETER OF PARTICLES IN MULTIPHASE SYSTEM

(71) Applicants: INSTITUTE OF PROCESS ENGINEERING, CHINESE ACADEMY OF SCIENCES, Beijing (CN); Nanjing Jiuzhang Chemical Technology Co., Ltd., Jiangsu (CN)

(72) Inventors: Chao Yang, Beijing (CN); Xiangyang Li, Beijing (CN); Guanqi Wang, Beijing (CN); Shifang Yang, Beijing (CN); Zaisha Mao, Beijing (CN)

(73) Assignees: INSTITUTE OF PROCESS ENGINEERING, CHINESE ACADEMY OF SCIENCES (CN); NANJING JIUZHANG CHEMICAL TECHNOLOGY CO., LTD. (CN)

( * ) Notice: Subject to any disclaimer, the term of this patent is extended or adjusted under 35 U.S.C. 154(b) by 136 days.

(21) Appl. No.: 15/368,838

(22) Filed: Dec. 5, 2016

(65) Prior Publication Data

US 2017/0299382 A1    Oct. 19, 2017

(30) Foreign Application Priority Data

Apr. 19, 2016  (CN) .......................... 2016 1 0245330

(51) Int. Cl.
*H04N 7/18*  (2006.01)
*G01B 21/10*  (2006.01)
(Continued)

(52) U.S. Cl.
CPC ............ *G01B 21/10* (2013.01); *G01B 11/105* (2013.01); *G01N 15/0227* (2013.01);
(Continued)

(58) Field of Classification Search
CPC ................................. G01B 21/10; H04N 9/045
(Continued)

(56) References Cited

U.S. PATENT DOCUMENTS 6,879,708 B2 * 4/2005 Wernet ...................... G06T 7/62
356/28
2006/0116531 A1 * 6/2006 Wonders ............... C07C 51/265
562/412
(Continued)

*Primary Examiner* — Richard T Torrente
(74) *Attorney, Agent, or Firm* — McDonald Hopkins LLC

(57) ABSTRACT

An online multiphase measuring method of concentration and diameter distribution of dispersed phase particles in a multiphase reactor is provided in the present invention. The method is based on an online multiphase measuring instrument. The method described herein includes the following steps: (1) the online multiphase measuring instrument is placed in a multiphase system, and an image of the particles in the multiphase system is obtained; (2) valid particles are determined as: the particle that its Grad(Φ) is greater than or equal to Grad(Φ$_{l/2}$) is labeled as a valid one; (3) the particle diameter is calculated by $d_i = 10 \times n_i / N_{10}$; according to the equation $$\alpha = \frac{V_c}{V} = \frac{\sum_i^n \frac{1}{6}\pi d_i^3}{S \times l},$$

the concentration of the valid particles is calculated. The concentration and diameter of bubbles, droplets or solid particles can be obtained in real time and online measurement. The accuracy of this method is high.

20 Claims, 5 Drawing Sheets

(51) Int. Cl.
*H04N 5/225* (2006.01)
*H04N 9/04* (2006.01)
*G01B 11/10* (2006.01)
*G01N 15/02* (2006.01)
*G01N 15/06* (2006.01)
*G06T 7/62* (2017.01)
*G01N 15/00* (2006.01)

(52) U.S. Cl.
CPC ............... G01N 15/06 (2013.01); G06T 7/62 (2017.01); H04N 5/2252 (2013.01); H04N 9/045 (2013.01); *G01N 2015/0053* (2013.01); *G01N 2015/0693* (2013.01); *G06T 2207/10024* (2013.01); *G06T 2207/10068* (2013.01)

(58) Field of Classification Search
USPC ........................................................ 348/137
See application file for complete search history.

(56) References Cited

U.S. PATENT DOCUMENTS

2011/0310270 A1* 12/2011 Gladnick ........... G01N 21/8806
348/229.1
2013/0057675 A1* 3/2013 Jaaskelainen ............. G01P 5/22
348/84

* cited by examiner (a)

(b)

(a)

(b)

(a)

(b)

(c)

ONLINE MEASURING METHOD OF CONCENTRATION AND DIAMETER OF PARTICLES IN MULTIPHASE SYSTEM

The present application claims priority to and the benefit of Chinese Patent Application No. 201610245330.6 filed on Apr. 19, 2016, the entire disclosure of which is incorporated herein by reference in its entirety.

TECHNICAL FIELD

The present invention belongs to the field of physical measuring technology, involving a new measuring method of concentration and diameter of dispersed phase particles in multiphase reactor, especially in two-phase or three-phase reactor.

BACKGROUND ART

In the field of chemical industry, metallurgy and environment, some complex multiphase flow processes are often involved in which there are one or two or more dispersed phases. It is urgent to solve the problem on the measurement of concentration and size distribution of dispersed phase particles in such a multiphase reactor.

At present, various probe methods are most commonly used based on optical fiber reflex or conductance (capacitance). Both methods have been applied successfully in the study of gas-liquid and liquid-solid systems, for example, the monofilament capacitance probe measurement system of phase containing rate and phase interface in multiphase pipe flow (CN 1865966A) and the measurement method and device of the two-phase flow parameter based on the double capacitance probe (CN 101413911A). However, both of them have some limits. Multiphase flow to be measured should be conductive for the conductance probe, while the fiber optic probe is very easy to be broken. Signals will interfere with each other when there are two or more dispersed phases. Sampling method is simple in principle and convenient in operation and can simultaneously measure the concentration and size distribution of dispersed particles. However, it is difficult to achieve the equivariant momentum condition needed for an accurate sampling measurement. At the same time, because it is an offline measurement, it is not applicable to non-steady processes. Particle size analyzer is used to measure solid particle size and its distribution and divided into settlement-type particle size analyzer, sedimentation balance, laser particle size analyzer, optical particle counter, resistance type particle counter and particle image analyzer etc. according to different measuring principles. In the process using a variety of particle size analyzer, it is often required to carry out the tedious sample preparation, so the particle size measuring method is not a real online measuring method.

Optical photography is the most intuitive measuring method. The outstanding advantage of non-intrusive photography is that it does not interfere with the flow field. And its shortcomings are that the measured reactors must be transparent or installed with viewports, and the holdup of bubbles or solid particles must be lower. Invasive photography such as optical fiber endoscope can be directly inserted into the reactor for online measurement. But the measurement accuracy is limited by the fiber diameter. At the same time, the wide-angle lens installed at the front end of the endoscope will cause a larger image distortion.

DISCLOSURE OF THE INVENTION

The aim of the present invention is to provide an online multiphase measuring method of concentration and diameter of dispersed phase particles in multiphase reactor. The concentration and diameter distribution of bubbles, droplets or solid particles can be obtained in real time and online measurement.

In order to achieve this goal, the present invention adopts the following technical scheme:

An online measuring method of concentration and diameter of particles in a multiphase system based on an immersion-type online multiphase measuring instrument, wherein the immersion-type online multiphase measuring instrument includes:

a package tube;

a viewport, sealedly installed at the front end of the package tube;

an illumination system for illuminating multiphase flow, including LED lamps and a brightness-adjustable light source connected with the LED lamps, which comprises a power supply, a signal generator and an oscilloscope;

a photographic system for taking pictures, including a telecentric lens and an image sensor;

a controller connected with the signal generator and the image sensor;

a signal processing and outputting system connected with the image sensor; and a display system connected with the signal processing and outputting system.

The LED lamps, the telecentric lens and the image sensor are located in the package tube and the exposure period of the image sensor is less than the pulse period of the signal generator, controlled by the controller.

The measuring method described herein includes the following steps:

(1) the immersion-type online multiphase measuring instrument is placed in a multiphase system, and an image of the particles in the multiphase system is obtained;

(2) valid particles are determined using the following steps: first, the focal plane position of the telecentric lens is determine; then, the object to be measured is respectively arranged on the front of the package tube, the l/2 positions ahead of or behind the focal plane, where l is the telecentric lens depth of field in mm; the object to be measured is photographed by the online multiphase measuring instrument, and the image of the object is obtained and the gray gradient Grad($\Phi_{l/2}$) around the boundary of the object is determined, where $\Phi_{l/2}$ is the gray value at the ±l/2 positions ahead of or behind the focal plane; if Grad($\Phi$) is greater than or equal to Grad($\Phi_{l/2}$), the particle is labeled as a valid one; and (3) the actual length of individual pixel is determined and the number of pixels occupied by the valid particle is measured, so the diameter of the valid particle $d_i$ is a product of the number of pixels occupied by the valid particle and the actual length of individual pixel; according to the equation $$\alpha = \frac{V_c}{V} = \frac{\sum_i^n \frac{1}{6}\pi d_i^3}{S \times l},$$

the concentration of the valid particles is calculated, where S is the effective area of the photosensitive area of the image sensor in mm$^2$; l is the telecentric lens depth of field in mm; $d_i$ is the particle diameter in mm; $V_c$ is the total volume of the valid particles, V is the volume of the measured area; n is the number of the valid particles.

The S value is determined by the model of the selected image sensor, and the 1 value is determined by the model of the telecentric lens.

The measuring method of the present invention uses an immersion-type online multiphase measuring instrument based on telecentric photography. And the online multiphase measuring instrument can produce unique parallel light path, and the image obtained is almost without distortion. Furthermore, the telecentric lens with long distance makes the probe extend everywhere in the reactor to take pictures. By designing appropriate operating procedures and image processing methods, real-time and online measurement of concentration and diameter distribution of high dispersed phase in two-phase or three-phase reactor can be realized.

As depicted in Step (1), when the particles in the multiphase system are light-colored opaque solid particles, reflection light of the solid surface is of great differences with that of the surrounding medium. Sharp images can be obtained by lighting in the same direction, controlling the synchronization of the pulse cycle of the signal generator and the exposure cycle of the image sensor.

The synchronization of the pulse cycle of the signal generator and the exposure cycle of the image sensor mainly comprises the following steps:

(a) according to the system to be measured and the surrounding environment, the output current of the power of the brightness-adjustable light source in the online multiphase measuring instrument is regulated, and the wavelength and period of pulse signal by the signal generator and oscilloscope are displayed;

(b) the exposure time, light balance, frame rate and gain of image capture are set by the controller; and (c) the synchronization of the pulse light and the image capture is realized by controlling the pulse period of the illumination signal larger than the exposure time of the image sensor by the controller.

Because the differences of reflection light between dark solid particles, bubbles or droplets and the surrounding medium is so small that sharp image of particles is difficult to be achieved only by lighting in the same direction. Therefore, as the measured particles are dark solid particles, bubbles or liquid droplets in Step (1), a reflecting plate is installed in the opposite to the viewport of the online multiphase measuring instrument in addition to lighting in the same direction, controlling the synchronization of the pulse cycle of the signal generator and the exposure cycle of the image sensor.

The distance between the reflecting plate and the front face of the online multiphase measuring instrument is greater than the depth of field of the telecentric lens, such as 1.2, 1.4, 1.6, 1.8, 2.0 or 2.5 times of the depth of field of the telecentric lens.

The distance between the reflecting plate and the front face of the online multiphase measuring instrument is 1.5 times of the depth of field of the telecentric lens.

The size of the reflecting plate is the same as that of the valid photosensitive area of the image sensor.

The reflecting plate is a square plate with a central protrusion.

The surface of the reflecting plate is bright white or silver white color.

The method determining the focal plane position in Step (2) is that: a graduated ruler with an accuracy of at least 0.1 mm (such as 0.05 mm, 0.02 or 0.01 mm) is placed in the same medium with the multiphase system; the medium is photographed using the online multiphase measuring instrument, the distance between the graduated ruler and the immersion-type online multiphase measuring instrument is adjusted and the clarity of the graduated ruler in the photograph is observed; the position where the graduated ruler is clearest is the focal plane position.

The method determining the actual length of individual pixel in Step (3) is that: a graduated ruler with an accuracy of at least 0.1 mm is arranged on the front of the online multiphase measuring instrument; then its image is captured; the number of pixels $N_{10}$ corresponding to 10 mm distance in the graduated ruler is picked up by an image processing software so as to determine the actual length of individual pixel. The image processing software can also pick up the number of pixels corresponding to the 20 mm, 30 mm, 40 mm, 45 mm or 50 mm distance in the graduated ruler.

The image processing software is Plus Image-Pro.

The diameter of the valid particle is calculated by $d_i = 10 \times n_i/N_{10}$, where $d_i$ is the particle diameter in mm; $n_i$ is the number of pixels occupied by the valid particle; $N_{10}$ is the number of pixels occupied by the 10 mm-long scale in the graduated ruler.

The work distance of the telecentric lens is 250-550 mm in order that the probe can achieve everywhere in the multiphase reactor, such as 260 mm, 300 mm, 350 mm, 380 mm, 420 mm, 470 mm, 550 mm and so on, and the depth of field is 1-3.7 mm, such as 1.2 mm, 1.5 mm, 1.8 mm, 2.0 mm, 2.2 mm, 2.5 mm, 2.8 mm, 3.0 mm or 3.5 mm and so on.

In order to disturb the flow field as less as possible, the magnification of the telecentric lens can be abandoned a little. Preferably, the magnification of the telecentric lens is 0.5-1 time, such as 0.6 times, 0.7 times, 0.8 times or 0.9 times.

The external diameter of the telecentric lens is 19-25 mm, such as 20 mm, 21 mm, 22 mm, 23 mm or 24 mm, etc.

The image sensor is a CCD camera or a CMOS camera.

The exposure time of the CCD camera or CMOS camera is less than or equal to 1 ms, such as 0.1 ms, 0.5 ms, 1 ms and so on. The resolution of it is 5-15 μm, such as 10 μm, 12 μm, 14 μm, 15 μm and so on. The number of pixels in length and width is at least 800×600, such as 2560×1920, 2048×1536, 1600×1200, 1280×1024, 800×600 and so on. The frame frequency is at least 60 fps, such as 60 fps, 100 fps, 150 fps, 200 fps, 1000 fps and so on.

The LED lamps are inside the package tube, while the brightness-adjustable light source is outside. Pulse light with various wavelengths for different multiphase systems is obtained by adjusting the light source. The number of the LED lamps is at least 12, such as 12, 16, 20, 24 and so on.

The LED lamps are evenly arranged circularly in the package tube, preferably. The internal diameter of the circular LED lamps should be as small as possible in the premise of the brightness.

The LED lamps are linked with the brightness-adjustable light source through wires.

The package tube is composed of a front tube and a back tube with different diameters.

The external diameter of the front tube is 25-30 mm, such as 25 mm, 26 mm, 28 mm and so on, and the length is 300-600 mm, such as 320 mm, 350 mm, 400 mm, 450 mm, 500 mm, 550 mm, 600 mm and so on, preferably. Specific size of the front tube can be determined according to the parameters of the selected telecentric lens by one skilled in the art.

The external diameter of the back tube is 50 mm, and the length is 50 mm, preferably. Specific size of the back tube can be determined according to the size of the selected image sensor by one skilled in the art.

The material of the package tube is stainless steel.

The viewport, LED lamps and telecentric lens are packaged in the front tube. The viewport is arranged on the end of the front tube away from the back tube, followed by the LED lamps and telecentric lens and the image sensor (CCD or CMOS camera) is packaged in the back tube.

The viewport is made up of a piece of circular glass coated by antireflection film inside, which can make sure the light transmittance over 95%.

The image sensor and the controller are connected by a high-speed data line to realize high speed transmission of the image.

The display system comprises an LED screen. It is used to display a signal received from a signal processing and outputting system.

The signal processing and outputting system, the controller and the display system are integrated into a computer. The computer can realize the functions of the signal processing and output system, controller and display system.

Compared with the prior technologies, the present invention has the following beneficial effects:

The present invention provides an online measuring method of concentration and diameter of dispersed phase particles in multiphase system, especially in two-phase or three-phase reactor using a multiphase measuring instrument based on telecentric photography. The concentration and diameter distribution of bubbles, droplets or solid particles can be obtained in real time and online measurement. The measurement accuracy is higher, and the particle diameter measurement error is less than 3% and the concentration error is less than 10%.

BRIEF DESCRIPTION OF THE DRAWINGS

As shown in FIG. 1, "1" is a stirred tank; "2" is a shaft of stirred tank; "3" is a baffle; "4" is an impeller; "5" is a solid particle; "6" is a bubble; "7" is a photography probe; "8" is a pulse light source; "9" is an image acquisition computer.

EMBODIMENTS

Further description of the technical scheme is as follows by specific examples combining with the drawings.

Figure 1:
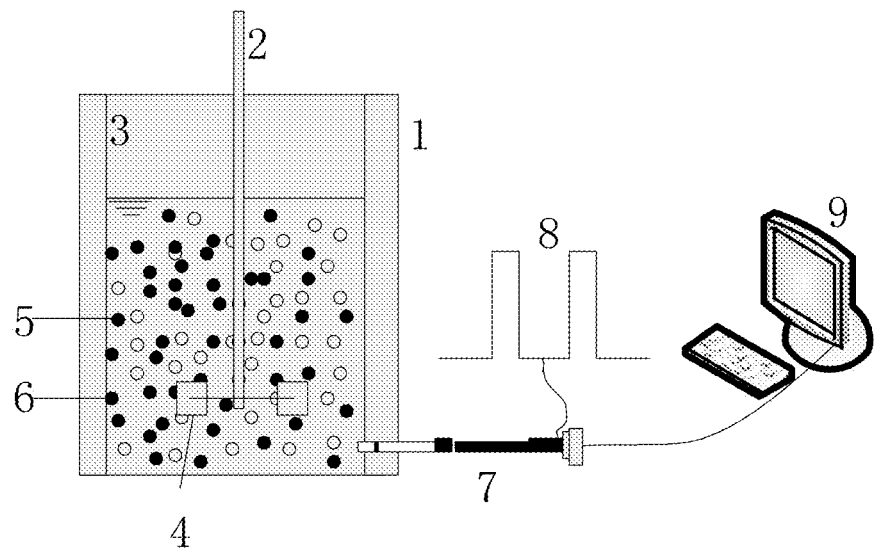
FIG. 1 is an experimental device measuring the diameter and the concentration of particles in a multiphase system by an immersion-type online multiphase measuring instrument provided by one embodiment of the present invention.

An experimental device measuring the diameter and the concentration of particles in a multiphase system by an immersion-type online multiphase measuring instrument is shown in FIG. 1.

The immersion-type online multiphase measuring instrument includes:
  a stainless steel package tube;
  a viewport, sealedly installed at the front end of the package tube;
  an illumination system for illuminating multiphase flow, including LED lamps and a brightness-adjustable light source connected with the LED lamps, which comprises a power supply, a signal generator and an oscilloscope;
  a photographic system for taking pictures, including a telecentric lens and an image sensor;
  a controller connected with the signal generator and the image sensor;
  a signal processing and outputting system connected with the image sensor; and
  a display system connected with the signal processing and outputting system.

The LED lamps, the telecentric lens and the image sensor are located in the stainless steel package tube to compose a photography probe 7, the brightness-adjustable light source, the controller, the signal processing and outputting system and the display system are located outside the stainless steel package tube, and the exposure period of the image sensor is less than the pulse period of the signal generator, controlled by the controller.

The signal processing and outputting system, the controller and the display system are integrated into an image acquisition computer.

Specifically, the first element is a viewport, which is a piece of circular sapphire glass coated by antireflection film. Twenty LED lamps are arranged uniformly behind the viewport, which composes a ring. A telecentric lens is installed behind the LED lamps, and the parameters are listed as: the magnification is 1; both vision fields of objects and images are φ8 mm; the work distance is 250 mm; the telecentricity is less than 0.1°; the depth of field is 2.1 mm; the resolution is 14.3 μm and the optical aberration is less than 0.12%. A work distance is between the outside surface of the viewport and the front side of the telecentric lens, in order to take sharp pictures. A standard C port connects the telecentric lens to the high speed CMOS. Parameters of the CMOS camera are that the resolution is 1280×1024, the colors are monochrome, the frame rate is 150 fps and a USB 3.0 is applied. The viewpoint, the LED lamps, the telecentric lens and the high speed CMOS camera are packaged inside the stainless steel tube. A brightness-adjustable light source is configured outside of the measuring instrument, connecting to the LED lamps by a wire. The telecentric lens connects to the image acquisition computer 9 by USB3.0 data line, and the computer is equipped with high speed image acquisition card.

Figure 2:
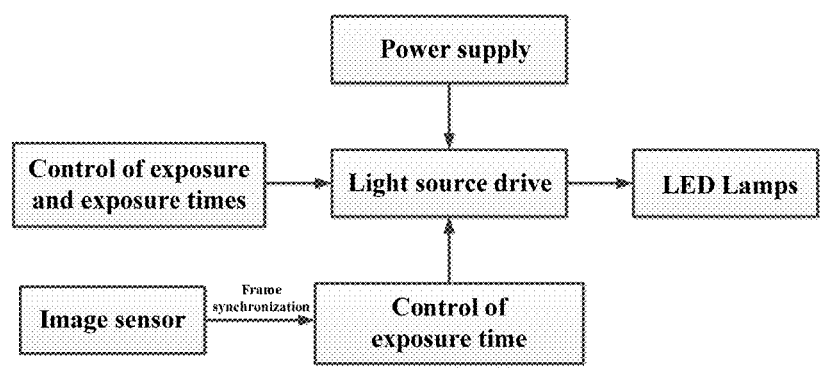
FIG. 2 is a synchronization control mode of lighting flash and CCD camera provided by one embodiment of the present invention.

In order to obtain a clear image by such an instrument, the way to control the synchronization of LED lamps flashing and CCD camera is shown in FIG. 2: opening source switch, then setting the intensity and period of pulse light by the light source driver, next, setting the exposure time, light balance, frame rate and gain to match the pulse period of the illumination signal and the exposure time of the image sensor (the exposure period of the image sensor is less than the pulse period of the signal generator) by the controller in computer. Thus, the synchronization of pulse light and image capturing is realized.

The experiment is conducted in a stirred tank 1 which is arranged with a stirring shaft 2 and an impeller 3 for heterogeneous mixing.

Example 1

The particle diameter distribution of solid particles in liquid-solid system is measured by the immersion-type online multiphase measuring instrument.

The experiment is carried out in the stirred tank which is described in FIG. 1. The solid particles are white plastic beads with a diameter of about 1 mm, and the average solid holdup (volume ratio) is 0.01. The measuring point is at r=0.07 m and z=0.055 m. The impeller speed is set as 480 rpm.

Figure 3:
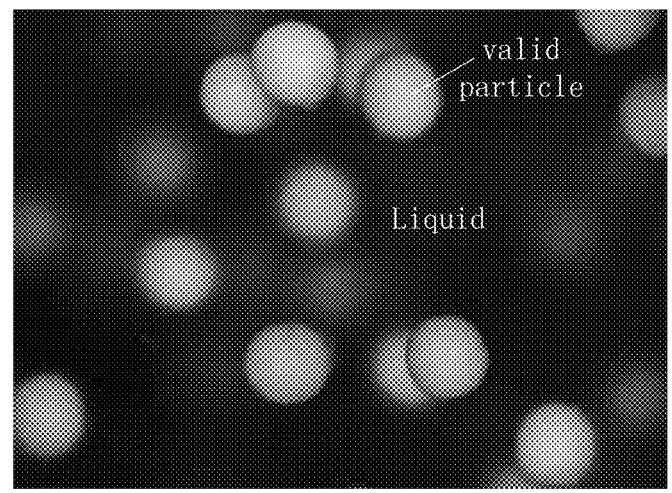
FIG. 3 is a typical particle image of the liquid-solid system captured by the immersion-type online multiphase measuring instrument in Example 1, where FIG. 3-(a) is a typical instantaneous particle image and FIG. 3-(b) is the measuring results of the solid particle diameter distribution.
Figure 3:
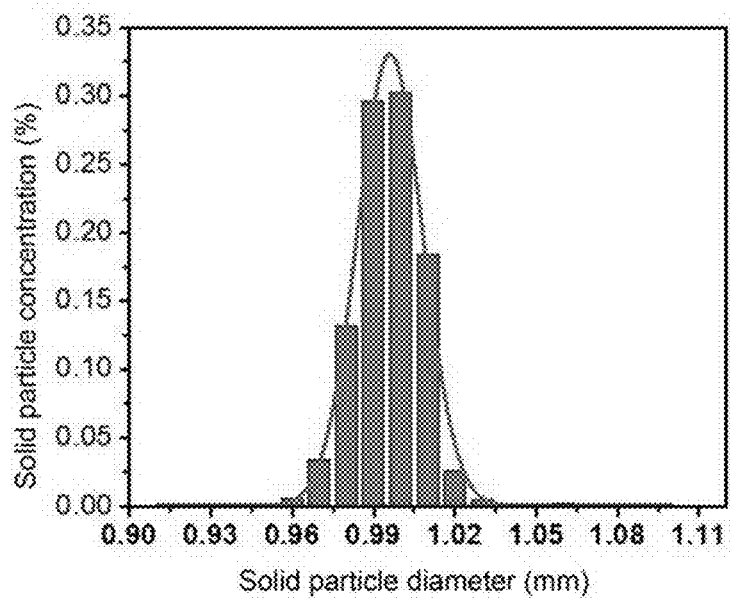

The measuring method comprises the following steps:

(1) the online multiphase measuring instrument is arranged in the liquid-solid system, and an image of the particles in the system is obtained as shown in FIG. 3-(a);

(2) valid particles are determined using the following steps:

First, the focal plane position of the telecentric lens is determined: a graduated ruler with an accuracy of 0.1 mm is placed in the same medium with the system; the medium is photographed using the online multiphase measuring instrument, the distance between the graduated ruler and the online multiphase measuring instrument is adjusted and the clarity of the graduated ruler in the photograph is observed; the position where the graduated ruler is clearest is the focal plane position;

then, the object to be measured is respectively arranged on the front of the package tube, the l/2 positions ahead of or behind the focal plane, where l is the telecentric lens depth of field (mm);

the object to be measured is photographed by the online multiphase measuring instrument, and the image of the object is obtained and the gray gradient Grad($\Phi_{l/2}$) around the boundary of the object is determined, where $\Phi_{l/2}$ is the gray value at the ±l/2 positions ahead of or behind the focal plane; if Grad($\Phi$) is greater than or equal to Grad($\Phi_{l/2}$), the particle is labeled as a valid one; and (3) a graduated ruler with an accuracy of at least 0.1 mm is arranged on the front of the online multiphase measuring instrument; then its image is captured; the number of pixels $N_{10}$ corresponding to 10 mm distance in the graduated ruler is picked up by an image processing software so as to determine the actual length of individual pixel; and the number of pixels occupied by the valid particle is measured;

the diameter of the valid particle is calculated by $d_i$=10× $n_i/N_{10}$, where $d_i$ is the particle diameter in mm; $n_i$ is the number of pixels occupied by the valid particle; $N_{10}$ is the number of pixels occupied by the 10 mm-long scale in the graduated ruler;

according to the equation $$\alpha = \frac{V_c}{V} = \frac{\sum_i^n \frac{1}{6}\pi d_i^3}{S \times l},$$

the concentration of the valid particles is calculated, where S is the effective area of the photosensitive area of the image sensor in mm²; l is the telecentric lens depth of field in mm; $d_i$ is the particle diameter in mm; $V_c$ is the total volume of the valid particles, V is the volume of the measured area; n is the number of the valid particles.

The solid particle diameter distribution at the measuring point is gained by analyzing nearly 4000 particles, and the results are shown in FIG. 3-(b), which are very close to the actual size of solid particles. The diameter of solid particles is in the range of 0.9-1.1 mm. The concentration of solid particles at this point is 0.0112, which is close to 0.0109 that obtained by a solid concentration instrument (PC-6a) and the error is merely 2.75%.

Example 2

The diameter distribution of bubbles in the gas-liquid system is measured by the immersion-type online multiphase measuring instrument.

The experiment is carried out in the stirred tank which is described in FIG. 1. The measuring point is at r=0.07 m and z=0.055 m. The air is vented by an annular gas distributor at a rate of flow of 800 L/h. The impeller speed is set as 450 rpm.

Figure 4:
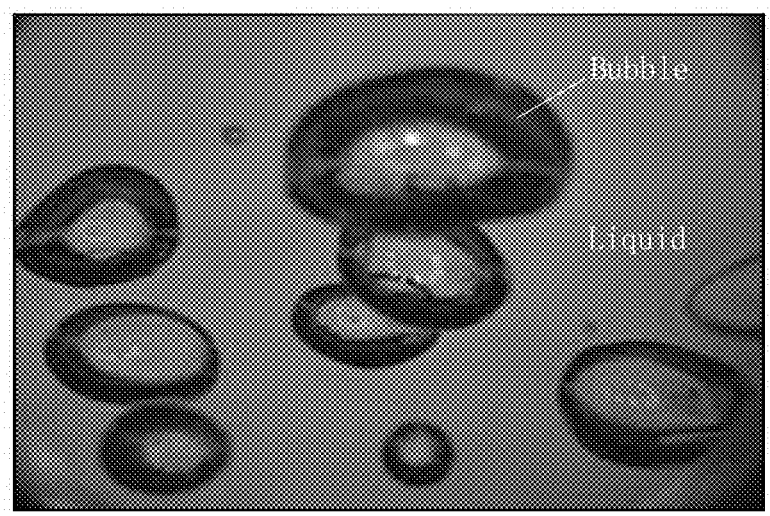
FIG. 4 is a typical particle image of the gas-liquid system captured by the immersion-type online multiphase measuring instrument in Example 2, where FIG. 4-(a) is a typical instantaneous bubble image and FIG. 4-(b) is the measuring results of the bubble diameter distribution.
Figure 4:
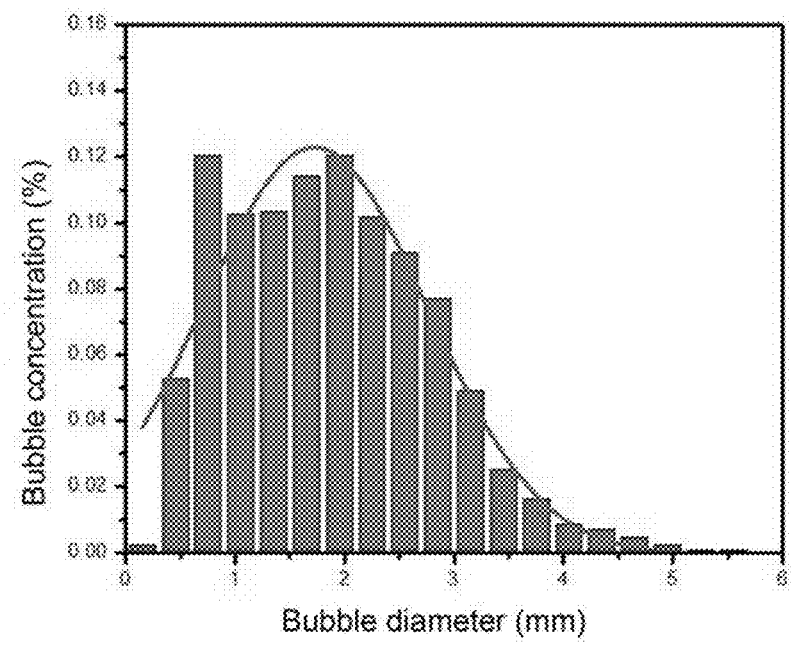

The measuring method comprises the following steps:

(1) the online multiphase measuring instrument is arranged in the gas-liquid system, and an image of the particles in the system is obtained as shown in FIG. 4-(a);

(2) valid particles are determined using the following steps:

First, the focal plane position of the telecentric lens is determined: a graduated ruler with an accuracy of 0.1 mm is placed in the same medium with the system; the medium is photographed using the online multiphase measuring instrument, the distance between the graduated ruler and the online multiphase measuring instrument is adjusted and the clarity of the graduated ruler in the photograph is observed; the position where the graduated ruler is clearest is the focal plane position;

then, the object to be measured is respectively arranged on the front of the package tube, the l/2 positions ahead of or behind the focal plane, where l is the telecentric lens depth of field (mm); the object to be measured is photographed by the online multiphase measuring instrument, and the image of the object is obtained and the gray gradient Grad($\Phi_{l/2}$) around the boundary of the object is determined, where $\Phi_{l/2}$ is the gray value at the ±l/2 positions ahead of or behind the focal plane; if Grad($\Phi$) is greater than or equal to Grad($\Phi_{l/2}$), the particle is labeled as a valid one; and (3) a graduated ruler with an accuracy of at least 0.1 mm is arranged on the front of the online multiphase measuring instrument; then its image is captured; the number of pixels $N_{10}$ corresponding to 10 mm distance in the graduated ruler is picked up by image processing software so as to determine the actual length of individual pixel; and the number of pixels occupied by the valid particle is measured;

the diameter of the valid particle is calculated by $d_i$=10× $n_i/N_{10}$, where $d_i$ is the particle diameter in mm; $n_i$ is the number of pixels occupied by the valid particle; $N_{10}$ is the number of pixels occupied by the 10 mm-long scale in the graduated ruler;

according to the equation $$\alpha = \frac{V_c}{V} = \frac{\sum_i^n \frac{1}{6}\pi d_i^3}{S \times l},$$

the concentration of the valid particles is calculated, where S is the effective area of the photosensitive area of the image sensor in mm²; l is the telecentric lens depth of field in mm;

$d_i$ is the particle diameter in mm; $V_c$ is the total volume of the valid particles, V is the volume of the measured area; n is the number of the valid particles.

Compared with solid particles, bubbles are more easily deformed. Nearly 4000 bubbles are analyzed, and the results are shown in FIG. 4-(b). The diameter of bubbles is mainly in the range of 1-3 mm. The concentration of bubbles at this point is 0.022.

Example 3

The particle diameter distribution of solid particles and bubbles in the gas-liquid-solid three-phase stirred tank is measured by the immersion-type online multiphase measuring instrument.

The experiment is carried out in the stirred tank which is described in FIG. 1. The material and volume of solid particle is the same to that used in Example 1, and ventilation conditions are the same as that used in Example 2. The impeller speed is set as 480 rpm. The position of the measuring point setting is the same to those in Examples 1 and 2.

Figure 5:
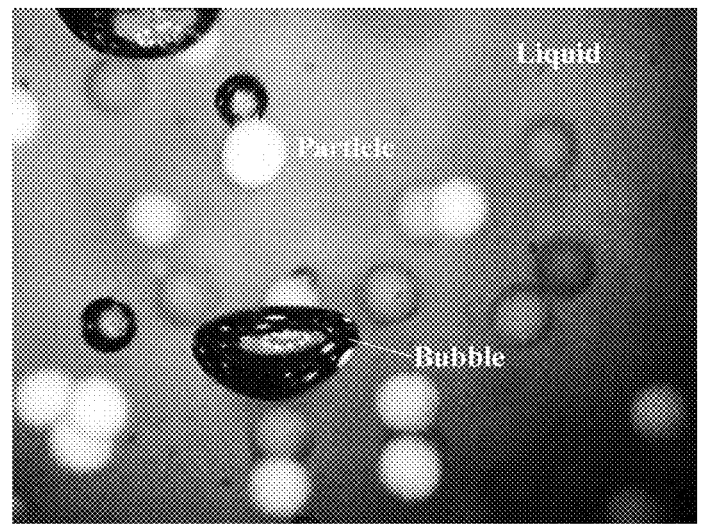
FIG. 5 is a typical particle image of the gas-liquid-solid system captured by the immersion-type online multiphase measuring instrument in Example 3, where FIG. 5-(a) is a typical instantaneous image and FIG. 5-(b) is the measuring results of the solid particle diameter distribution and FIG. 5-(c) is the measuring results of the bubble diameter distribution.
Figure 5:
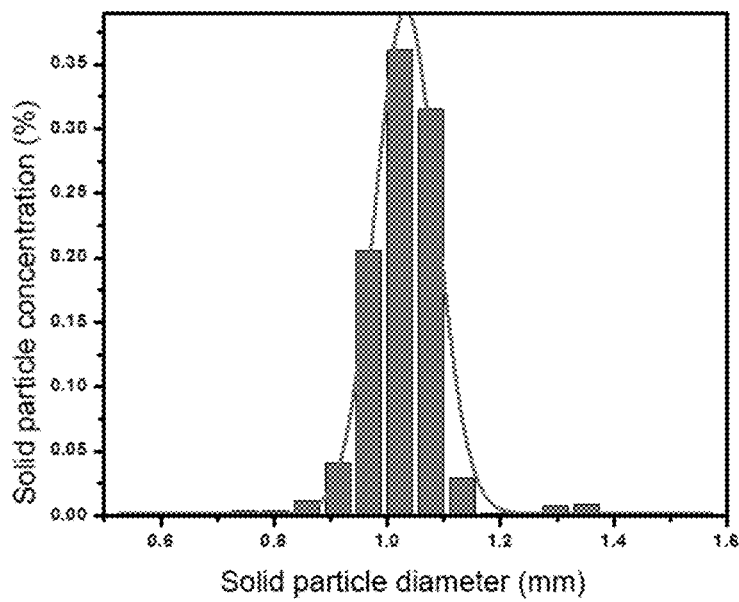
Figure 5:
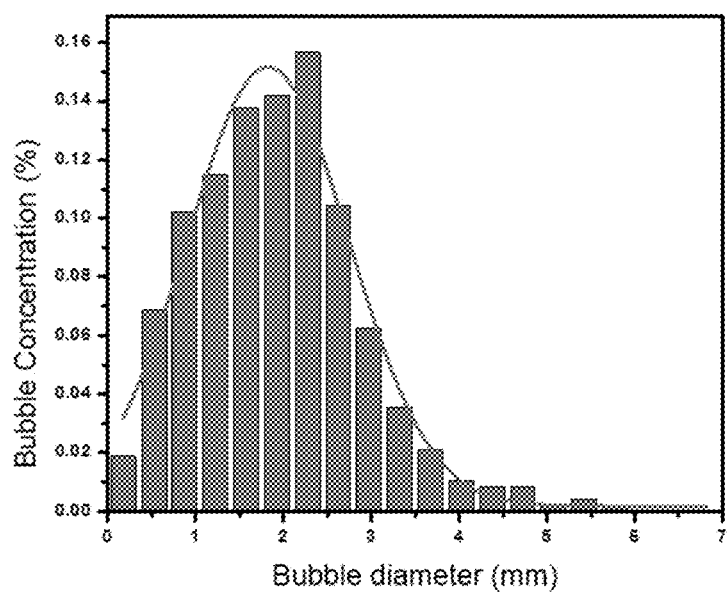

The measuring method comprises the following steps:

(1) the online multiphase measuring instrument is arranged in the gas-liquid-solid system, and an image is obtained as shown in FIG. 5-(a);

(2) valid particles are determined using the following steps:

First, the focal plane position of the telecentric lens is determined: a graduated ruler with an accuracy of 0.1 mm is placed in the same medium with the system; the medium is photographed using the online multiphase measuring instrument, the distance between the graduated ruler and the online multiphase measuring instrument is adjusted and the clarity of the graduated ruler in the photograph is observed; the position where the graduated ruler is clearest is the focal plane position;

then, the object to be measured is respectively arranged on the front of the package tube, the l/2 positions ahead of or behind the focal plane, where l is the telecentric lens depth of field (mm); the object to be measured is photographed by the online multiphase measuring instrument, and the image of the object is obtained and the gray gradient $Grad(\Phi_{l/2})$ around the boundary of the object is determined, where $\Phi_{l/2}$ is the gray value at the ±l/2 positions ahead of or behind the focal plane; if $Grad(\Phi)$ is greater than or equal to $Grad(\Phi_{l/2})$, the particle is labeled as a valid one; and (3) a graduated ruler with an accuracy of at least 0.1 mm is arranged on the front of the online multiphase measuring instrument; then its image is captured; the number of pixels $N_{10}$ corresponding to 10 mm distance in the graduated ruler is picked up by image processing software so as to determine the actual length of individual pixel; and the number of pixels occupied by the valid particle is measured;

the diameter of the valid particle is calculated by $d_i = 10 \times n_i/N_{10}$, where $d_i$ is the particle diameter in mm; $n_i$ is the number of pixels occupied by the valid particle; $N_{10}$ is the number of pixels occupied by the 10 mm-long scale in the graduated ruler;

according to the equation $$\alpha = \frac{V_c}{V} = \frac{\sum_i^n \frac{1}{6}\pi d_i^3}{S \times l},$$

the concentration of the valid particles is calculated, where S is the effective area of the photosensitive area of the image sensor in mm²; l is the telecentric lens depth of field in mm; $d_i$ is the particle diameter in mm; $V_c$ is the total volume of the valid particles, V is the volume of the measured area; n is the number of the valid particles.

Nearly 4000 bubbles are analyzed, and the results are shown in FIGS. 5-(b) and 5-(c). The diameter of solid particles is in the range of 0.9-1.1 mm and that of bubbles is in the range of 0.5-2.8 mm. The concentrations of bubbles and solid particles at this point are 0.016 and 0.0115 respectively.

The above are only specific examples of the present invention but the present invention is not limited thereto. Those skilled in the art to which the present invention belongs should appreciate that any change or replacement which can be easily thought by those skilled in the art within the technical scope disclosed by the present invention all fall into the scope protected and disclosed by the present invention.

The invention claimed is:

1. An online measuring method of concentration and diameter of particles in multiphase system, based on an immersion-type online multiphase measuring instrument comprising:

a package tube;

a viewport, sealedly installed at a front end of the package tube;

an illumination system for illuminating multiphase flow, including LED lamps and a brightness-adjustable light source connected with the LED lamps, which comprises a power supply, a signal generator and an oscilloscope;

a photographic system for taking pictures, including a telecentric lens and an image sensor;

a controller connected with the signal generator and the image sensor;

a signal processing and outputting system connected with the image sensor;

a display system connected with the signal processing and outputting system;

the LED lamps, the telecentric lens and the image sensor are located in the package tube and the exposure period of the image sensor is less than the pulse period of the signal generator, controlled by the controller;

wherein, the measuring method comprises the following steps:

(1) the immersion-type online multiphase measuring instrument is arranged in a multiphase system, and an image of particles in the multiphase system is obtained;

(2) valid particles are determined using the following steps:

first, the focal plane position of the telecentric lens is determined; then, an object to be measured is respectively arranged on the front of the package tube, the l/2 positions ahead of or behind the focal plane, where l is the telecentric lens depth of field in mm;

the object to be measured is photographed by the online multiphase measuring instrument, and the image of the object is obtained and a gray gradient $Grad(\Phi_{l/2})$ around the boundary of the object is determined, where $\Phi_{l/2}$ is a gray value at the ±l/2 positions ahead of or behind the focal plane; if $Grad(\Phi)$ is greater than or equal to $Grad(\Phi_{l/2})$, the particle is labeled as a valid one;

(3) the actual length of individual pixel is determined and the number of pixels occupied by the valid particle is measured, so the diameter of the valid particle $d_i$ is a product of the number of pixels occupied by the valid particle and the actual length of individual pixel;
according to the equation $$\alpha = \frac{V_c}{V} = \frac{\sum_i^n \frac{1}{6}\pi d_i^3}{S \times l},$$

the concentration of the valid particles is calculated, where S is the effective area of the photosensitive area of the image sensor in (mm$^2$; l is the telecentric lens depth of field in mm; $d_i$ is the particle diameter in mm; $V_c$ is the total volume of the valid particles, V is the volume of the measured area; n is the number of the valid particles.

2. The method according to claim 1, wherein in Step (1), when the particles in the multiphase system are dark solid particles, bubbles or liquid droplets, a reflecting plate is installed when taking pictures; the particles to be measured are placed between the reflecting plate and the online multiphase measuring instrument.

3. The method according to claim 2, wherein the distance between the reflecting plate and the online multiphase measuring instrument is greater than the depth of field of the telecentric lens;
the distance between the reflecting plate and the front face of the online multiphase measuring instrument is 1.5 times of the depth of field of the telecentric lens.

4. The method according to claim 2, wherein the size of the reflecting plate is the same as that of the valid photosensitive area of the image sensor.

5. The method according to claim 2, wherein the reflecting plate is a square plate with a central protrusion;
the surface of the reflecting plate is bright white or silver white color.

6. The method according to claim 1, wherein the method determining the focal plane position in Step (2) is that: a graduated ruler with an accuracy of at least 0.1 mm is placed in the same medium with the multiphase system; the graduated ruler is photographed using the online multiphase measuring instrument, the distance between the graduated ruler and the online multiphase measuring instrument is adjusted and the clarity of the graduated ruler in the photograph is observed; the position where the graduated ruler is clearest is the focal plane position.

7. The method according to claim 1, wherein the method determining the actual length of individual pixel in Step (3) is that: a graduated ruler with an accuracy of at least 0.1 mm is arranged on the front of the online multiphase measuring instrument; then its image is captured; the number of pixels $N_{10}$ corresponding to 10 mm distance in the graduated ruler is picked up by an image processing software so as to determine the actual length of individual pixel.

8. The method according to claim 7, wherein the image processing software is Plus Image-Pro.

9. The method according to claim 1, wherein the diameter of the valid particle is calculated by $d_i = 10 \times n_i/N_{10}$, where di is the particle diameter in mm; $n_i$ is the number of pixels occupied by the valid particle; $N_{10}$ is the number of pixels occupied by the 10 mm-long scale in the graduated ruler.

10. The method according to claim 1, wherein the work distance of the telecentric lens is 250-550 mm, and the depth of field is 1-3.7 mm;
the magnification of the telecentric lens is 0.5-1 time;
the external diameter of the telecentric lens is 19-25 mm.

11. The method according to claim 1, wherein the image sensor is a CCD camera or a CMOS camera;
the exposure time of the CCD camera or CMOS camera is less than or equal to 1 ms; the resolution is 5-15 μm; the number of pixels in length and width is at least 800×600; the frame frequency is at least 60 fps.

12. The method according to claim 1, wherein the number of the LED lamps is at least 12.

13. The method according to claim 1, wherein the LED lamps are evenly arranged circularly in the package tube;
the LED lamps are linked with the brightness-adjustable light source through wires.

14. The method according to claim 1, wherein the package tube is composed of a front tube and a back tube with different diameters.

15. The method according to claim 14, wherein the external diameter of the front tube is 25-30 mm and the length is 300-600 mm;
the external diameter of the back tube is 50 mm, and the length is 50 mm;
the material of the package tube is stainless steel.

16. The method according to claim 14, wherein the viewport, LED lamps and telecentric lens are packaged in the front tube; the viewport is arranged on the end of the front tube away from the back tube, followed by the LED lamps and telecentric lens; and the image sensor is packaged in the back tube.

17. The method according to claim 1, wherein the viewport is made up of a piece of circular glass coated by antireflection film inside.

18. The method according to claim 1, wherein the image sensor and the controller are connected by a high-speed data line.

19. The method according to claim 1, wherein the display system comprises a LED screen.

20. The method according to claim 1, wherein the signal processing and outputting system, the controller and the display system are integrated into a computer.

* * * * *